US007031602B2

(12) United States Patent
Faries, Jr. et al.

(10) Patent No.: US 7,031,602 B2
(45) Date of Patent: Apr. 18, 2006

(54) METHOD AND APPARATUS FOR CONTROLLING TEMPERATURE OF INFUSED LIQUIDS

(75) Inventors: Durward I. Faries, Jr., Las Vegas, NV (US); Bruce R. Heymann, Vienna, VA (US); David Hendrix, Ashburn, VA (US)

(73) Assignee: Patented Medical Solutions, LLC, Las Vegas, NV (US)

( * ) Notice: Subject to any disclaimer, the term of this patent is extended or adjusted under 35 U.S.C. 154(b) by 83 days.

(21) Appl. No.: 10/683,155

(22) Filed: Oct. 14, 2003

(65) Prior Publication Data

US 2004/0170409 A1    Sep. 2, 2004

Related U.S. Application Data

(63) Continuation-in-part of application No. 10/095,100, filed on Mar. 12, 2002.

(60) Provisional application No. 60/417,655, filed on Oct. 11, 2002, provisional application No. 60/275,256, filed on Mar. 12, 2001.

(51) Int. Cl.
*A61F 7/00* (2006.01)

(52) U.S. Cl. ....................... 392/470; 392/471; 604/110

(58) Field of Classification Search ........ 392/470–471; 604/110–115
See application file for complete search history.

(56) References Cited

U.S. PATENT DOCUMENTS

| 1,659,719 A | 2/1928 | Blake |
|---|---|---|
| 1,847,573 A | 3/1932 | Rupp |
| 2,175,099 A | 10/1939 | Abbott |
| 2,214,215 A | 9/1940 | Watermann et al. |
| 2,576,874 A | 11/1951 | Acton |
| 2,713,112 A | 7/1955 | Mills et al. |
| 2,741,099 A | 4/1956 | Beane |
| 2,841,132 A | 7/1958 | Philipp |
| 2,885,526 A | 5/1959 | Paulding |
| 2,994,760 A | 8/1961 | Pecoraro et al. |
| 3,051,582 A | 8/1962 | Muckler et al. |
| 3,193,339 A | 7/1965 | Cooper |
| 3,241,603 A | 3/1966 | Nagata |
| 3,255,812 A | 6/1966 | Bayane et al. |

(Continued)

FOREIGN PATENT DOCUMENTS

DE          37 42 927 A1       7/1989

(Continued)

OTHER PUBLICATIONS

Cahill, *New Name, New Helmsman*, JEMS, Aug. 1996.

(Continued)

*Primary Examiner*—Thor S. Campbell
(74) *Attorney, Agent, or Firm*—Edell, Shapiro & Finnan, LLC

(57) ABSTRACT

A system for controlling the temperature of intravenous fluids according to the present invention includes a heating cabinet and a power supply cabinet. The heating cabinet includes a housing, a flexible cover and a heating plate with a generally curved configuration to uniformly heat a solution container. The cover wraps around the fluid container to secure the solution container against the heating cabinet. The heating cabinet further includes a heating controller to maintain the solution at a desired temperature. The power supply cabinet provides power to the heating cabinet and includes a display for indicating a solution temperature. A secondary power supply may be provided in the heating cabinet to facilitate heating controller operation when the heating cabinet is disengaged from the power supply cabinet. The system further monitors and provides reports of fluid temperature history.

49 Claims, 3 Drawing Sheets

U.S. PATENT DOCUMENTS

| | | |
|---|---|---|
| 3,329,202 A | 7/1967 | Birman |
| 3,353,589 A | 11/1967 | Tope et al. |
| 3,386,498 A | 6/1968 | Funfstuck |
| 3,485,245 A | 12/1969 | Lahr et al. |
| 3,536,132 A | 10/1970 | Pecoraro et al. |
| 3,590,215 A | 6/1971 | Anderson et al. |
| 3,612,165 A | 10/1971 | Haynes |
| 3,713,302 A | 1/1973 | Reviel |
| 3,777,187 A | 12/1973 | Kohn |
| 3,801,278 A | 4/1974 | Wagner et al. |
| 3,826,035 A | 7/1974 | Fishman |
| 3,858,106 A | 12/1974 | Launius |
| 3,879,171 A | 4/1975 | Tulis |
| 3,940,742 A | 2/1976 | Hudspeth et al. |
| 4,024,377 A | 5/1977 | Henke |
| 4,084,080 A | 4/1978 | McMahan |
| 4,090,514 A | 5/1978 | Hinck et al. |
| 4,098,123 A | 7/1978 | Granzow, Jr. |
| 4,167,663 A | 9/1979 | Granzow, Jr. et al. |
| 4,189,995 A | 2/1980 | Löhr et al. |
| 4,233,495 A | 11/1980 | Scoville et al. |
| 4,309,592 A | 1/1982 | Le Boeuf |
| 4,318,276 A | 3/1982 | Sato et al. |
| 4,328,676 A | 5/1982 | Reed |
| 4,331,859 A | 5/1982 | Thomas et al. |
| 4,336,435 A | 6/1982 | Kashyap et al. |
| 4,364,234 A | 12/1982 | Reed |
| 4,407,133 A | 10/1983 | Edmonson |
| 4,419,568 A | 12/1983 | Van Overloop |
| 4,430,078 A | 2/1984 | Sprague |
| 4,455,478 A | 6/1984 | Guibert |
| 4,464,563 A | 8/1984 | Jewett |
| 4,476,877 A | 10/1984 | Barker |
| 4,481,410 A | 11/1984 | Bortnick |
| 4,495,402 A | 1/1985 | Burdick et al. |
| 4,523,078 A | 6/1985 | Lehmann |
| 4,551,136 A | 11/1985 | Mandl |
| 4,585,441 A | 4/1986 | Archibald |
| 4,605,840 A | 8/1986 | Koopman |
| 4,628,186 A | 12/1986 | Bergemann et al. |
| 4,647,756 A | 3/1987 | Willis |
| 4,657,004 A | 4/1987 | Coffey |
| 4,678,460 A | 7/1987 | Rosner |
| 4,680,445 A | 7/1987 | Ogawa |
| 4,684,367 A | 8/1987 | Schaffer et al. |
| 4,707,587 A | 11/1987 | Greenblatt |
| 4,726,193 A | 2/1988 | Burke et al. |
| 4,745,248 A | 5/1988 | Hayes |
| 4,747,450 A | 5/1988 | Ikegame et al. |
| 4,801,777 A | 1/1989 | Auerbach |
| 4,808,159 A | 2/1989 | Wilson |
| 4,823,554 A | 4/1989 | Trachtenberg et al. |
| 4,832,689 A | 5/1989 | Mauerer et al. |
| 4,874,033 A | 10/1989 | Chatelain et al. |
| 4,883,117 A | 11/1989 | Dobbs et al. |
| 4,894,207 A | 1/1990 | Archer et al. |
| 4,906,816 A | 3/1990 | Van Leerdam |
| 4,910,386 A | 3/1990 | Johnson |
| 4,923,681 A | 5/1990 | Cox et al. |
| 4,934,336 A | 6/1990 | White |
| 4,935,604 A | 6/1990 | Allen et al. |
| 4,961,320 A | 10/1990 | Gutmann |
| 4,994,021 A | 2/1991 | Smith et al. |
| 5,013,889 A | 5/1991 | Bakke |
| 5,061,241 A | 10/1991 | Stephens, Jr. et al. |
| 5,061,630 A | 10/1991 | Knopf et al. |
| 5,073,167 A | 12/1991 | Carr et al. |
| 5,081,697 A | 1/1992 | Manella |
| 5,106,373 A | 4/1992 | Augustine et al. |
| 5,108,372 A | 4/1992 | Swenson |
| 5,125,069 A * | 6/1992 | O'Boyle ..................... 392/465 |
| 5,125,900 A | 6/1992 | Teves |
| 5,153,827 A | 10/1992 | Coutre et al. |
| 5,183,994 A | 2/1993 | Bowles, Sr. et al. |
| 5,195,976 A | 3/1993 | Swenson |
| 5,217,064 A | 6/1993 | Kellow et al. |
| 5,243,172 A | 9/1993 | Hazan et al. |
| 5,243,833 A | 9/1993 | Coelho et al. |
| 5,245,693 A | 9/1993 | Ford et al. |
| 5,250,032 A | 10/1993 | Carter, Jr. et al. |
| 5,263,323 A | 11/1993 | Maus et al. |
| 5,263,929 A | 11/1993 | Falcone et al. |
| 5,276,310 A | 1/1994 | Schmidt et al. |
| 5,282,264 A | 1/1994 | Reeves et al. |
| 5,296,684 A | 3/1994 | Essig et al. |
| 5,297,234 A | 3/1994 | Harms et al. |
| 5,308,335 A | 5/1994 | Ross et al. |
| 5,315,830 A | 5/1994 | Doke et al. |
| 5,333,326 A | 8/1994 | Faries, Jr. et al. |
| 5,345,923 A | 9/1994 | Luebke et al. |
| 5,364,385 A | 11/1994 | Harms et al. |
| 5,381,510 A | 1/1995 | Ford et al. |
| 5,397,875 A | 3/1995 | Bechtold, Jr. |
| 5,399,007 A | 3/1995 | Marconet |
| 5,408,576 A | 4/1995 | Bishop |
| 5,420,962 A | 5/1995 | Bakke |
| 5,424,512 A | 6/1995 | Turetta et al. |
| 5,433,704 A | 7/1995 | Ross et al. |
| 5,483,799 A | 1/1996 | Dalto |
| 5,572,873 A | 11/1996 | Lavigne et al. |
| 5,584,811 A | 12/1996 | Ross et al. |
| RE35,501 E | 5/1997 | Ross et al. |
| 5,653,905 A | 8/1997 | McKinney |
| 5,658,478 A | 8/1997 | Roeschel et al. |
| 5,661,978 A | 9/1997 | Holmes et al. |
| 5,681,284 A | 10/1997 | Herskowitz |
| 5,720,728 A | 2/1998 | Ford |
| 5,729,653 A | 3/1998 | Magliochetti et al. |
| 5,733,263 A | 3/1998 | Wheatman |
| 5,743,878 A | 4/1998 | Ross et al. |
| 5,786,568 A | 7/1998 | McKinney |
| 5,875,282 A | 2/1999 | Jordan et al. |
| 5,879,329 A | 3/1999 | Ginsburg |
| 5,910,210 A | 6/1999 | Violi et al. |
| 5,924,289 A | 7/1999 | Bishop, II |
| 5,935,099 A * | 8/1999 | Peterson et al. ............... 604/65 |
| 5,954,700 A | 9/1999 | Kovelman |
| 5,961,492 A | 10/1999 | Kriesel et al. |
| 5,977,520 A | 11/1999 | Madson, Jr. et al. |
| 5,986,239 A | 11/1999 | Corrigan, III et al. |
| 5,989,238 A | 11/1999 | Ginsburg |
| 6,035,102 A | 3/2000 | Bakke |
| 6,039,926 A | 3/2000 | Goldman |
| 6,045,648 A | 4/2000 | Palmgren et al. |
| 6,096,007 A | 8/2000 | Haan et al. |
| 6,117,122 A | 9/2000 | Din et al. |
| 6,124,572 A | 9/2000 | Spilger et al. |
| 6,129,702 A | 10/2000 | Woias et al. |
| 6,174,300 B1 | 1/2001 | Kriesel et al. |
| 6,175,099 B1 | 1/2001 | Shei et al. |
| 6,221,045 B1 | 4/2001 | Duchon et al. |
| 6,221,051 B1 | 4/2001 | Hjertman et al. |
| 6,248,077 B1 | 6/2001 | Elson et al. |
| 6,254,572 B1 | 7/2001 | Knipfer et al. |
| 6,259,067 B1 | 7/2001 | Faries, Jr. et al. |
| 6,294,762 B1 | 9/2001 | Faries, Jr. et al. |
| 6,316,750 B1 | 11/2001 | Levin |
| 6,376,805 B1 | 4/2002 | Faries, Jr. et al. |
| 6,384,380 B1 | 5/2002 | Faries, Jr. et al. |
| 6,467,953 B1 | 10/2002 | Faries, Jr. et al. |
| 6,566,631 B1 | 5/2003 | Faries, Jr. et al. |
| 6,649,040 B1 | 11/2003 | Mirchi et al. |

| | | |
|---|---|---|
| 6,660,974 B1 | 12/2003 | Faries, Jr. et al. |
| 6,722,782 B1 | 4/2004 | Faries, Jr. et al. |
| 6,740,059 B1 | 5/2004 | Flaherty |
| 6,748,164 B1 | 6/2004 | Kuzyk |
| 6,768,085 B1 | 7/2004 | Faries, Jr. et al. |
| 6,824,528 B1 | 11/2004 | Faries, Jr. et al. |
| 2002/0184906 A1 | 12/2002 | Faries, Jr. et al. |
| 2003/0000939 A1 | 1/2003 | Faries, Jr. et al. |
| 2003/0114795 A1 | 6/2003 | Faries, Jr. et al. |
| 2003/0135388 A1 | 7/2003 | Martucci et al. |
| 2004/0170409 A1 | 9/2004 | Faries et al. |
| 2004/0189258 A1 | 9/2004 | Lehmann et al. |

FOREIGN PATENT DOCUMENTS

| | | |
|---|---|---|
| DE | 197 52 578 A1 | 6/1999 |
| WO | WO 98/38953 A1 | 9/1998 |
| WO | WO 98/45658 A1 | 10/1998 |

OTHER PUBLICATIONS

CBi Healthcare System, Inc., *Controlled Temperature Cabinet System*, JEMS, Mar. 1997.

Koolatron, *P-34 PC-3 Precision Control Thermoelectric Cooler/Warmer*, Jan. 1998.

Koolatron, *Canadian company announces the release of a precision control unit*, Aug. 1997.

Anton, *500 miles from nowhere. it'll give you a cold drink or a warm burger . . .* , Technology Update, 1993.

Koolatron, *1997 U.S. $ Price List*, 1997.

Kellow et al, *Drug Adulteration In Prehospital Emergency Medical Services*, Oct. 1994.

CBi Medical, Inc., *IV Fluid Warmer Model 8362*, 1992.

* cited by examiner

METHOD AND APPARATUS FOR CONTROLLING TEMPERATURE OF INFUSED LIQUIDS

CROSS-REFERENCE TO RELATED APPLICATIONS

This application is a Continuation-in-Part of U.S. patent application Ser. No. 10/095,100, entitled "Method and Apparatus for Controlling Pressurized Infusion and Temperature of Infused Liquids" and filed Mar. 12, 2002, which claims priority from U.S. Provisional Patent Application Serial No. 60/275,256, entitled "Method and Apparatus for Controlled Pressure Infusion and Temperature of Infused Liquids" and filed Mar. 12, 2001. In addition, the present application claims priority from U.S. Provisional Patent Application Serial No. 60/417,655, entitled "Method and Apparatus for Controlling Temperature of Infused Liquids" and filed Oct. 11, 2002. The disclosures of the above-mentioned patent applications are incorporated herein by reference in their entireties.

BACKGROUND OF THE INVENTION

1. Technical Field

The present invention pertains to temperature control systems for infused liquids, such as the types disclosed in U.S. patent application Ser. Nos. 09/380,507, entitled "Method and Apparatus for Pressure Infusion and Temperature Control of Infused Liquids" and filed Apr. 24, 2000, and Ser. No. 10/095,100, entitled "Method and Apparatus for Controlling Pressurized Infusion and Temperature of Infused Liquids" and filed Mar. 12, 2002, the disclosures of which are incorporated herein by reference in their entireties. In particular, the present invention is directed toward a portable system that controls the temperature of a fluid within a flexible bag or container during infusion of the fluid from the container to a patient.

2. Discussion of Related Art

Generally, various items are required to be heated prior to use in a medical procedure, or in support of related medical care, to prevent injury to a patient. These items typically include intravenous solutions, irrigation fluids, surgical instruments, bottles, and blankets. Intravenous (IV) fluids, for example, are typically stored in a cool environment and, consequently, require heating to precise temperatures to prevent thermal shock and injury from occurring during infusion of the fluid into a patient. Similarly, irrigation fluids can be warmed or cooled to various temperatures depending upon their intended use. These types of fluids are typically provided to a patient utilizing a flexible bag or container filled with the fluid and delivered via a fluid line that conveys the fluid from the bag to the patient.

Some medical items can only be heated for a limited period of time, or in accordance with controlled warming cycles, in order to avoid adversely affecting their effectiveness. For example, some fluids, such as whole blood or fluids containing medication, should be warmed evenly to a specific temperature and can be rendered unusable or unsafe if all or a portion of the fluid is overheated.

In order to provide the necessary heated items for use in medical procedures, the related art provides several devices for regulating temperature of a fluid in an IV fluid bag. For example, U.S. Pat. No. 4,430,078 (Sprague) discloses a portable blood infusion pump designed to be employed in combination with a blood bag. The blood bag is located within a storage chamber that includes an inflatable bladder. Pressurized fluid is conducted within the inflatable bladder to press against the blood bag to enable discharge of the blood from the blood bag through a discharge conduit assembly. A container containing a supply of the pressurized fluid is mounted within the pump housing and is connected to the inflatable bladder. A pressure regulator is disposed in the housing to permit variance of pressure applied by the bladder against the blood bag in response to user manipulation of a knob. The pressure level applied by the bladder to the blood bag may be preset by a user via the knob while the regulator maintains the pressure level and automatically provides additional gas to the bladder in response to decreasing quantities of blood within the blood bag. An electrical heater apparatus may be included within the device to provide heat energy to the blood bag so as to warm the blood prior to being infused into a patient.

U.S. Pat. No. 5,125,900 (Teves) discloses a device for heating and pressurizing fluid filled containers. The device wraps around a flexible bag containing fluid to warm the fluid and to pressurize the bag so that warm fluid flows from the bag at a rate dependent upon the amount of pressure applied to the bag. The device includes a heating element that may be set at a preselected temperature and an inflatable bladder that may be inflated to a preselected pressure.

U.S. Pat. No. 5,420,962 (Bakke) discloses a system for warming blood or other liquids to body temperature for infusion into a patient. The system includes a blood warmer apparatus having a pair of closely spaced apart heat transfer plates, each of which forms one face of a housing containing flat vapor condensation heating units. A flat disposable heat exchanging blood warming envelope is held clamped between the heat transfer plates. An air heating unit in one of the apparatus housings includes a cool air inlet, heat transfer fins on the walls of the vapor condensation heater unit, a fan and guides for conducting air past those fins and a warmed air outlet. An external elongated insulated air hose is connected at one end to the warmed air outlet and extends to the patient. The blood flow line from the outlet of the heat exchanging envelope is positioned within the warmed air hose to maintain the physiologic temperature of the blood.

U.S. Pat. No. 5,733,263 (Wheatman) discloses an apparatus for heating fluid contained in one or more bags and delivering the fluid from at least one bag to a surgical patient. The apparatus includes a housing to enclose at least one bag containing fluid and having a door positioned to provide access to the housing interior. The apparatus further includes an inflatable bladder mounted in the housing interior and connected to a source of pressurized fluid for inflation. The inflatable bladder exerts force against at least one bag mounted within the housing. A regulator permits regulation of gas pressure to the bladder in response to user manipulation of a housing regulator knob. In addition, the apparatus includes a heater mounted adjacent the housing door in heat transfer relationship with the fluid and at least one bag.

U.S. Pat. Nos. 5,879,329 and 5,989,238 (Ginsburg) disclose a system for infusing a fluid into a patient. The system includes a fluid reservoir and a temperature-altering device in close proximity thereto. The temperature-altering device is employed to heat or cool the fluid to a desired temperature. A positive pressure device in the form of a bladder and pressure source may be provided to place the reservoir under positive pressure while at the desired temperature. The pressure source may be connected to a processor to control the total rate and volume of fluid introduced into the bladder, thereby controlling the rate and volume of fluid leaving the reservoir. A transfer member is further provided to transfer at least some of the fluid into the patient while at the desired temperature. In addition, the system may be portable for utilization in field applications.

U.S. Pat. No. 6,035,103 (Bakke) discloses a system for warming blood or other liquids to body temperature and maintaining the liquid at that temperature for infusion into a patient. The system includes a cylindrical condensation liquid heating chamber having an inner tubular air heater. A cylindrical heat retaining shell surrounds and is spaced from the outer wall of the heating chamber. A flat flexible heat exchanging liquid warming envelope is held clamped between the outer wall of the heating chamber and the surrounding shell. An external outer elongated air hose is connected at one end to a warmed air outlet from the air heater and extends to the patient and surrounds an inner elongated warm liquid flow line to maintain the temperature of the liquid.

U.S. Pat. No. 6,096,007 (Haan et al.) discloses a pressure container for applying pressure to a flexible bag received therein and filled with a medical fluid in order to deliver the fluid from the flexible bag. The pressure container includes a housing that has an opening for introduction of the bag, a cover for covering the opening, an aperture for leading a fluid discharge line of the bag out of the pressure container and a closure for sealed joining of the cover and housing. The housing may be configured as an upright hollow-cylindrical body closed at the bottom and open at the top, the cross-section of which has a flattened, oval shape and corresponds roughly to the cross-sectional contour of a bag. The two opposing large-area upright housing sidewalls each have, in mirror-image fashion, the shape of a segment of a cylindrical shell with lateral ends joined by joining segments. A heater may be provided on the housing.

The related art devices described above suffer from several disadvantages. In particular, the Teves and Haan et al. devices heat a particular bag surface or do not completely enclose a fluid bag within the device, thereby enabling skewed or non-uniform heating of IV fluid within the bag. Similarly, the Wheatman apparatus employs a heating element assembly located on the housing door that provides heat to one surface of the IV bag. These types of heating typically produce "hot" and/or "cold" spots within the IV fluid that may cause patients to receive the fluid at inappropriate temperatures, thereby risking injury to those patients.

In addition, the Bakke (U.S. Pat. Nos. 5,420,962 and 6,035,103), Sprague, Wheatman and Ginsburg devices typically house an IV fluid bag within a housing. Thus, these devices do not permit easy access and/or viewing of the bag during infusion. This typically requires medical personnel to repeatedly access the housing interior to monitor the bag (e.g., to determine the amount of fluid remaining within the bag and whether or not the bag needs to be replaced with a new bag) and/or increases the amount of time needed to replace an existing depleted or problematic bag with a new bag. The increased time needed to replace a bag may cause serious adverse conditions for a patient, especially during critical medical situations. In addition, the above devices do not provide a medical item temperature history. This enables use of medical items that may have been rendered unsafe or less effective during heating due to attainment of undesirable temperatures, thereby increasing risk of injury to a patient.

OBJECTS AND SUMMARY OF THE INVENTION

Accordingly, it is an object of the present invention to control the temperature of fluids being infused into a patient.

It is another object of the present invention to facilitate easy access to and visual monitoring of a medical fluid container disposed within a temperature controlled infusion system.

Yet another object of the present invention is to uniformly heat IV fluid to a desired temperature within a temperature controlled infusion system.

Still another object of the present invention is to facilitate heating of a medical solution container during transport.

A further object of the present invention is to monitor and provide reports of medical fluid temperature during operation of a temperature controlled infusion system.

The aforesaid objects may be achieved individually and/or in combination, and it is not intended that the present invention be construed as requiring two or more of the objects to be combined unless expressly required by the claims attached hereto According to the present invention, a system for controlling the temperature of intravenous fluids includes a heating cabinet and a power supply cabinet coupled to the heating cabinet. The heating cabinet includes a housing, a heating plate and a flexible cover. The heating plate includes a generally curved or arcuate configuration to surround and uniformly heat fluid within a solution container placed thereon. The cover wraps around a portion of the fluid container to secure the solution container against the heating cabinet. The heating cabinet further includes a heating controller to maintain the solution container at a desired temperature. The power supply cabinet provides power to the heating cabinet and includes a temperature display for indicating a temperature of the solution container being heated within the heating cabinet. A secondary power supply (e.g., a battery) may also be provided in the heating cabinet to facilitate heating controller operation and heating of the solution container when the heating cabinet is disengaged from the power supply cabinet. The system further monitors and provides reports of fluid temperature history.

The above and still further objects, features and advantages of the present invention will become apparent upon consideration of the following detailed description of specific embodiments thereof, particularly when taken in conjunction with the accompanying drawings, wherein like reference numerals in the various figures are utilized to designate like components.

DETAILED DESCRIPTION OF THE PREFERRED EMBODIMENTS

Figure 1:
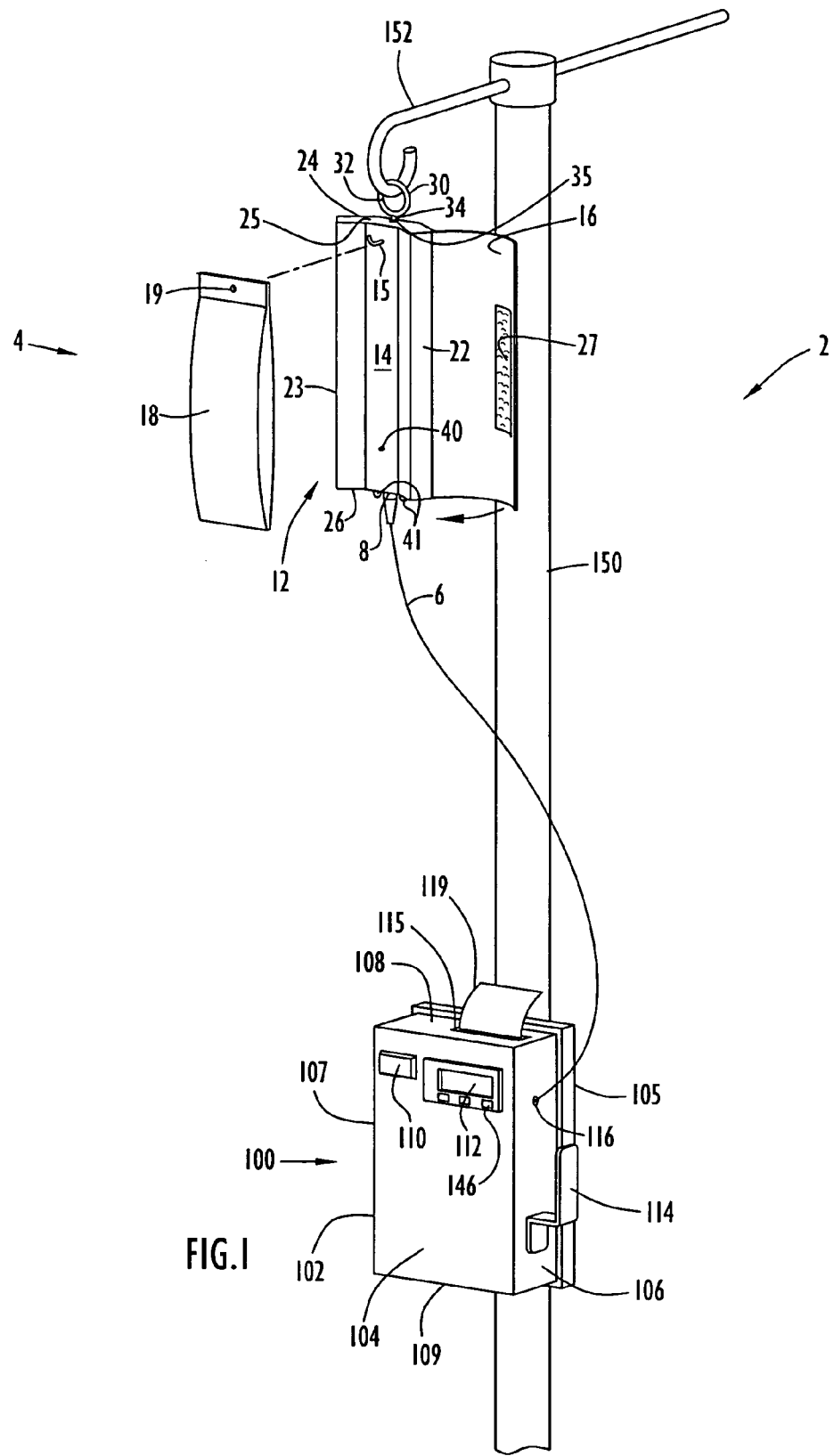
FIG. 1 is a view in perspective of a temperature controlled infusion system according to the present invention.

A temperature controlled infusion system 2 according to the present invention is illustrated in FIG. 1. Specifically, system 2 includes a heating cabinet 4 and a power supply cabinet 100 that is coupled to heating cabinet 4 via a power supply cord 6 to supply electrical power to the heating cabinet during system operation as described below. While the heating and power supply cabinets are illustrated in FIG. 1 as being secured to an IV pole 150, it is noted that the system may be secured to any suitable support member (e.g., an operating table, a wall surface, etc.).

Heating cabinet 4 receives a solution container 18 (e.g., an intravenous fluid bag, a blood bag, a container with a solution used for irrigation (e.g., a container with a solution used in transurethral resection of the prostate procedures), etc.). The heating cabinet includes a housing 12, a heating plate 14 recessed within the housing, and a cover or flap 16 that wraps around at least a portion of solution container 18 to secure it to the heating plate. Heating plate 14 has a generally curved or arcuate configuration to conform to or surround the solution container and thereby evenly distribute heat to the container. The heating plate is further suitably dimensioned to engage and provide heat to a variety of different sized solution containers. The heating plate includes at least one heating plate section or panel (e.g., a middle and two side panels) to apply heat to the solution container. The housing includes sidewalls 22, 23 extending from opposing longitudinal edges of the heating plate to a rear wall section 24 that is dimensioned to generally conform to the arcuate profile of the heating plate. Top and bottom walls 25, 26 extend between the respective upper and lower edges of the heating plate, housing sidewalls, and rear wall section, thus defining an enclosed housing interior of the heating cabinet. The housing is generally compact for easy portability. A heating control circuit, including heating control elements as described below, is disposed within the housing interior of the heating cabinet. The heating cabinet is configured for holding one or more solution bags of varying shapes and dimensions.

Heating plate 14 includes at least one heating pad disposed proximate the heating plate to apply heat to at least a portion of the plate sections surrounding the solution bag. The heating pad is preferably disposed on the surface of the heating plate that is within the housing interior to prevent direct contact between the heating pad and solution bag secured against the heating plate. Optionally, the heating plate may include any suitable number of heating pads disposed at selected locations to provide uniform heating along the heating plate.

Extending transversely from an upper portion of heating plate 14 near top wall 25 is a hook member 15. The hook member is suitably aligned on the heating plate to engage an aperture 19 in an upper portion of solution bag 18 so as to secure the solution bag in suitable alignment with the heating plate prior to engaging cover 16 with the solution bag as described below. Alternatively, the hook member may be provided on the top wall of the heating cabinet housing or at any other suitable location to facilitate appropriate alignment of the solution container with the heating plate.

A heating control circuit is disposed within the housing interior of heating cabinet 4 to control heating of the heating plate and thus the temperature of the solution bag in a manner described below. The heating control circuit includes a heating controller, a temperature controller that serves as a safety limit switch to turn off the heating controller if a threshold temperature of the heating plate is exceeded, a temperature sensor 40 and a power indicator 41 to provide an indication that the heating cabinet is receiving power from the power supply cabinet. Power indicator 41 includes one or more light emitting diodes (LEDs) extending from bottom wall 26 of the heating cabinet that provide an indication as to whether the heating cabinet is activated (i.e., the heating cabinet is receiving power from the power supply cabinet) to maintain the solution bag at the desired temperature. However, it is noted that the power indicator may be disposed at any suitable locations on the heating cabinet and may include any suitable number and type of indication devices (e.g., an LCD display) to indicate activation of the heating cabinet. Optionally, a secondary power source 160 (FIG. 4) may also be provided in the heating cabinet housing to facilitate operation of the heating cabinet in certain situations when the heating cabinet has been disconnected from the power supply cabinet as described below. A secondary power switch 162 (FIG. 4) may further be provided at any suitable location on the heating cabinet to facilitate activation and/or deactivation of the secondary power source.

Temperature sensor 40 extends through heating plate 14 at a suitable location to facilitate direct contact with the solution bag secured to the heating plate. The temperature sensor is preferably a resistive temperature-sensing device (e.g., a RTD sensor). However, it is noted that the temperature sensor may be of any suitable type for measuring the temperature of the solution bag. Optionally, the heating control circuit may further include any suitable type of display devices (e.g., an LCD display disposed on the heating cabinet housing) to display temperatures measured by the temperature sensor and/or any suitable type of input devices (e.g., buttons or keys disposed on the heating cabinet housing) to facilitate entry of a desired or setpoint temperature for the solution container and/or an excessive threshold temperature for the heating plate.

Cover 16 may be constructed of a substantially transparent conformable plastic material and is generally rectangular having a side edge secured to a first portion of housing rear wall section 24. The cover is flexible and includes a conventional hook-and-loop fastener 27 (e.g., VELCRO) disposed on the cover interior surface toward the cover unsecured end for engagement with a corresponding fastener (not shown) disposed on a second portion of the housing rear wall section that is separated from the first portion of the housing rear wall section to which the side edge of the cover is secured. The cover secures the solution bag against heating plate 14 to ensure the solution within the bag is maintained at the desired temperature during system operation. Preferably, cover 16 is suitably dimensioned to cover all or part of the heating plate when the cover is fastened to the second portion of the housing rear wall section.

The heating cabinet further includes an adjustable support member to releasably support the heating cabinet to an IV pole or other support structure in a variety of selected orientations during system operation. A support member 30 extends from top wall 25 of the heating cabinet housing and includes a ring 32 that releasably engages with a hook support member 152 extending transversely from an upper section of IV pole 150. A securing pin 34 connects the ring member to the cabinet housing top wall to permit the heating cabinet to be suspended from hook support member 152 of the IV pole during system operation. In particular, the securing pin is rotationally secured within a base 35 disposed in a locking recess that is within top wall 25 to permit full 360° rotation of the heating cabinet about the central axis of the securing pin and thus a variety of orientations of the heating cabinet with respect to the IV pole. In an exemplary embodiment, engagement of the securing pin within the base may include a swivel type connection. Optionally, engagement of the securing pin and base may include a ratchet-type connection, where base 35 includes a plurality of radially extending teeth and securing pin 34 includes a pawl or other suitable engaging member transversely extending from the securing pin to releasably lock between adjacent teeth of the recess during rotations of the heating cabinet with respect to the pin. Hook support member 152 of the IV pole further substantially limits or prevents rotational movement of support member 30 when the heating cabinet is rotated with respect to securing pin 34. Thus, the heating cabinet may be rotated in a variety of orientations with respect to the IV pole so as to permit selective alignment of the front portion of the heating cabinet with respect to the position of the user or medical personnel during system operation.

Disposed on bottom wall 26 of the heating cabinet housing is a power supply port 8 configured to receive an end of power supply cord 6. The power supply port is configured for releasable engagement with the power supply cord so as to permit disconnection of the heating cabinet from the power supply cabinet in the event that only the heating cabinet is to be transported along with a patient to another location. Alternatively, the power supply cord may be permanently secured to the power supply port of the heating cabinet. The heating cabinet may further include a retractable cord mechanism to retract the power cord into the heating cabinet for easy storage.

Figure 2:
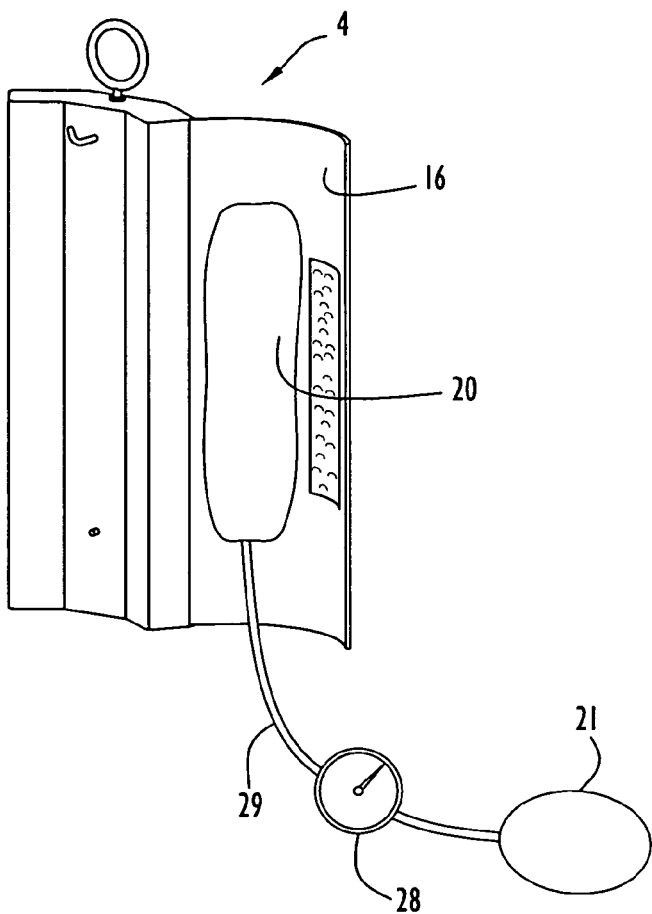
FIG. 2 is a view in perspective of an alternative embodiment of the heating cabinet of FIG. 1 including a cover with a bladder according to the present invention.

Cover 16 may include various devices to enhance infusion. Referring to FIG. 2, cover 16 may include an inflatable bellows or bladder 20 disposed on the cover interior surface to apply pressure to the solution bag to achieve a desired solution flow or infusion rate and to force the bag against the heating plate to warm the solution. The bellows is preferably coupled to a manual pump 21 (e.g., bulb) by a tube 29 to provide and maintain a desired pressure within the bellows to achieve a particular flow or infusion rate of solution. The pressure within the bellows may be displayed by a pressure gauge 28. Alternatively, the bellows may be coupled to a pump within the heating or power supply cabinets that automatically controls pressure within the bellows in accordance with preset or user provided flow rate settings. The bellows may be secured to the cover in any fashion and may be of any shape or size. For example, the upper portion of the bellows may include greater dimensions that those of the lower portion to provide a downward force against the solution bag for enhanced flow.

Figure 3:
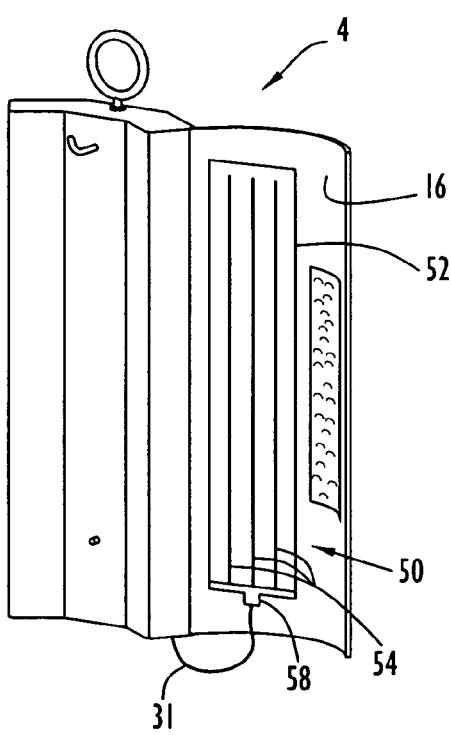
FIG. 3 is a view in perspective of another alternative embodiment of the heating cabinet of FIG. 1 including a cover with a heating element according to the present invention.

In addition, the cover may include a heating element 50 to apply heat to the solution bag front surface, thereby providing heat to substantially all sides of the bag. Referring to FIG. 3, heating element 50 is disposed on a cover interior surface in facing relation with heating plate 14. The heating element is preferably implemented by a clear or transparent acrylic heater including a sheet 52 with electrically conductive wiring 54 embedded therein. The transparent heating element enables viewing of the solution bag. Wiring 54 is arranged within sheet 52 and, hence, on the cover to coincide with the solution bag. By way of example only, the wiring is configured as a plurality of longitudinally extending parallel lines. However, any configuration coincident the solution bag may be employed. Wiring 54 further includes connection terminals 58 disposed toward a bottom edge of sheet 52 to connect to the heating control circuit via a wire 31 as described below. Alternatively, the heating element and/or wiring 54 may be formed integral with cover 16.

Referring back to FIG. 1, power supply cabinet 100 includes a generally rectangular housing 102 with a front wall 104, an opposing rear wall 105, opposing sidewalls 106, 107 and top and bottom walls 108, 109. A control circuit as described below is disposed within an interior housing defined by the front, rear, side, top and bottom walls of the power supply cabinet for providing power to the heating cabinet during system operation. The power supply cabinet includes a power switch 110 and display device 112 disposed on front wall 104 near the upper end of the power supply cabinet. The display device may be of any suitable type (e.g., an LCD display) to provide an indication of the solution bag temperature measured by the temperature sensor in the heating cabinet. Input devices 146 (e.g., buttons, keys, keypad, etc.) may be disposed proximate display 112 to facilitate entry of information (e.g., set points, thresholds, etc.) and control of the display.

The power supply cabinet further includes devices to measure, record and/or provide a report (e.g., hardcopy form or for display) of system conditions (e.g., time, date, temperature, etc.) as described below. The power supply cabinet includes a slot 115, preferably defined in top wall 108, to enable a hardcopy report 119 to be retrieved from the system by a user. However, the slot may be defined at any location on the power supply cabinet. The report provides medical personnel documentation for their files on the heating characteristics of the solution. The information may include the start date and start time of solution or other item heating, the time interval the solution or other item was heated, the temperature the solution or other item attained during heating and/or the time and temperature of the solution or other item when the solution was removed from the system (e.g., partial or complete history of time and solution or other item temperature). The report may further include a variety of information (e.g., facility name and location, patient information, doctor information, type of procedure, type of solution, items being heated, amount or quantity of solution or other item being heated, etc.).

A suitable connecting member (not shown) is provided on power supply cabinet rear wall 105 to secure the power supply cabinet to a support member. For example, the connecting member utilized in the system of FIG. 1 includes a pole-mounting clamp for securing cabinet 100 to IV pole 150. The pole-mounting clamp is configured to permit mounting of the power supply cabinet in a variety of selected orientations with respect to the IV pole so as to permit the front portion of the power supply cabinet to face the user during system operation. Alternatively, the connecting member may include a wall mounting or any other suitable connector for securing the cabinet directly to a wall or other surface. The rear wall of the power supply cabinet also includes a removable back panel to permit access to control circuit elements disposed within the power supply cabinet.

A power supply port 116 is disposed on sidewall 106 of the power supply cabinet housing and is configured to receive another end of power supply cord 6. The power supply port may be configured to releasably or permanently secure the power supply cord to the power supply cabinet. Sidewall 106 further includes a bracket 114 that provides a storage location for the power supply cord (e.g., when one or both ends of the cord are disengaged from the heating and/or power supply cabinets) and/or an outlet power cord for receiving power from a wall outlet (e.g., by wrapping the power supply cord around the bracket). Alternatively, the power supply cabinet may include one or more retractable cord mechanisms that retract the power supply cord and/or the outlet cord into the power supply cabinet for easy storage.

Figure 4:
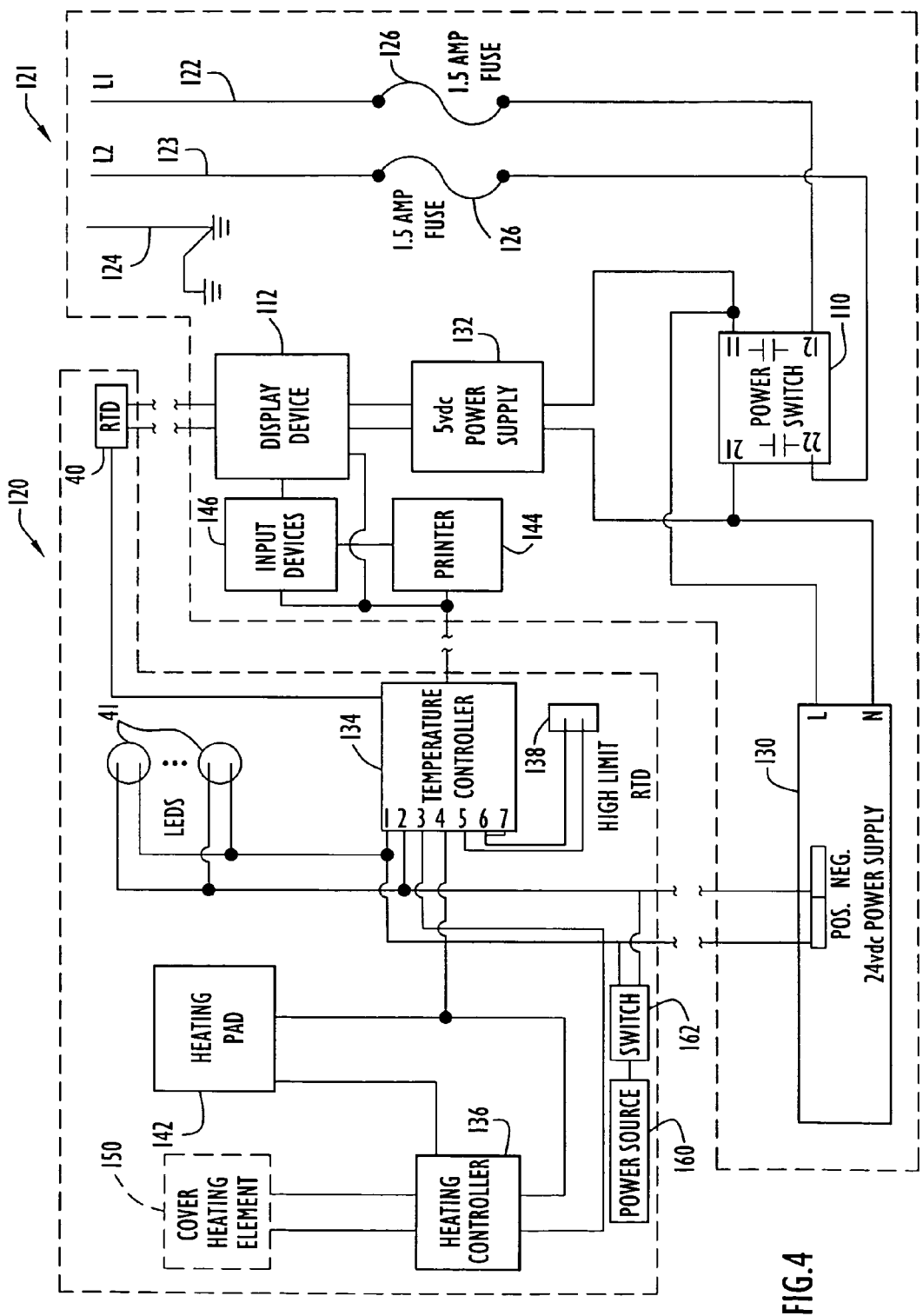
FIG. 4 is an electrical schematic diagram of an exemplary control circuit for the system of FIG. 1.

An exemplary control circuit for controlling system operation is illustrated in FIG. 4. The control circuit is divided into two dotted line sections to identify a heating control circuit 120 disposed in heating cabinet 4 and a power supply circuit 121 disposed in power supply cabinet 100, where the circuits are coupled as described below via power supply cord 6. Referring to power supply circuit 121, lines 122, 123, and 124 conduct power received from the outlet power cord (not shown) of power supply cabinet 100, where line 124 is connected to ground. Lines 122, 123 are each connected in series with a corresponding fuse 126, preferably a 1.5 amp fuse, to protect the circuit from power surges and spikes. Lines 122, 123 extend from fuses 126 to power switch 110 that controls power to the circuit. The power switch enables a main power supply 130 (e.g., a 24V dc power supply) to provide power to heating cabinet 4 via power supply cord 6. Power switch 110 further enables a display power supply 132 (e.g., a 5V dc power supply) to provide power to display device 112 in the power supply cabinet. Display device 112 may receive information from a temperature controller 134 or may include a controller to process signals received directly from various sensors (e.g., temperature sensor 40) for displaying measured information.

With reference to heating control circuit 120, temperature controller 134 disposed in the heating cabinet is connected to power supply 130 in the power supply cabinet via the power supply cord. Power may alternatively be supplied to the temperature controller from power source 160 (e.g., a battery) via switch 162 when the heating cabinet is disconnected from the power supply cabinet (e.g., during transport). The temperature controller is capable of measuring time to provide reports of solution temperature. The temperature controller is connected to a heating controller 136, a high limit temperature sensor 138, temperature sensor 40, power indicator 41 and heating pad 142 of circuit 120, and may further be coupled to a printer 144, input devices 146 and display device 112 within circuit 121 via cord 6. The power indicator is also connected to power supply 130. The power indicator preferably includes one or more LEDs disposed on the heating cabinet housing (as described above) to provide an indication that the heating cabinet is receiving power from the power supply cabinet and is operating to maintain the solution bag at the desired temperature.

Temperature sensor 40, which extends through heating plate 14, may be connected to display device 112 disposed in the power supply cabinet via power supply cord 6. The temperature sensor provides signals to display device 112 for displaying measured temperature information of the solution bag. Alternatively, the display device may receive the temperature information from temperature controller 134.

Heating controller 136 is connected to heating pad 142 and to heating element 150 of cover 16 (FIG. 2) when that heating element is employed. The heating controller is typically set to provide power to the heating pad and heating element to respectively maintain the heating plate and element at a predetermined temperature (e.g., about 43° C.). Optionally, the heating controller may further be connected with temperature sensor 40 to control the supply of power to the heating pad and heating element based upon temperature measurements of the solution bag by the temperature sensor. Temperature controller 134 controls power to the heating controller based on a temperature measurement of the heating plate by high limit temperature sensor 138. Temperature sensor 138, preferably a resistive temperature device (RTD), measures resistance through the heating plate and provides a temperature indication to temperature controller 134. The temperature controller disables power to heating controller 136 in response to the measured temperature by sensor 138 exceeding a predetermined excessive threshold temperature for the heating plate (e.g., a measured heating plate temperature exceeding 44° C. or other desired threshold temperature). In effect, this arrangement serves as a shut-off safety device to disable the heating plate and heating element in response to excessive heating plate temperatures. The heating element and heating pad may alternatively be controlled by respective individual controllers based on measured temperature values of the solution bag or other items (e.g., heating plate, heating element, heating pad, etc.).

Alternatively, heating controller 136 may be set to maintain the solution bag at a desired temperature that is entered by the user via input devices 146 disposed on the power supply cabinet near display device 112. Desired temperature information may be sent from the input devices to heating controller 136 via a circuit connection extending through the power supply cord to link these two components. The input devices may be connected to display device 112 to facilitate display of time, temperature, or other information entered by the user. Input devices 146 may further be connected to printer 144 to facilitate the printing of information processed by the control circuit. The heating controller may be configured to control power supplied to the heating pad and heating element based upon a comparison of the measured solution container temperature (e.g., provided to the heating controller by temperature sensor 40 via a connection within the heating control circuit) and the desired temperature. When the measured solution container temperature is below the desired temperature, the heating controller maintains or enables power to heating pad 142 and heating element 150. Conversely, if the measured solution bag temperature exceeds the desired temperature, the heating controller disables power to the heating pad and heating element. Thus, the heating controller may maintain the solution bag at a desired temperature entered by the user by enabling or disabling power to the heating pad and heating element.

Input devices 146 on the power supply cabinet may further facilitate entry of an excessive threshold temperature for the heating plate to control when the temperature controller enables or disables power to the heating controller. Specifically, the temperature controller may be connected to input devices 146 disposed on the power supply cabinet to facilitate a comparison of the heating plate temperature measured by high limit temperature sensor 138 and the excessive threshold temperature for the heating plate entered by the user in order to determine whether to shut off power to the heating controller. It is further noted that input devices may be disposed directly on the heating cabinet to facilitate the entry of desired temperature information to the heating controller and/or temperature controller. The heating controller may control any quantity of heating pads and/or heating elements, or the heating control circuit may employ a heating controller for each heating pad disposed on the heating plate and/or heating element to control the solution bag temperature in a substantially similar manner as described above.

Temperature controller 134 may be implemented by any conventional or other controller or microprocessor (e.g., chip, card, processor, circuitry, etc.) and receives various information (e.g., enablement of heating cabinet temperature, etc.) related to thermal treatment of the solution. The temperature controller may receive any additional information (e.g., facility information, doctor information, patient information, item (e.g., solution, instrument, etc.) information, etc.) from medical personnel or users via input devices 146.

The temperature controller further maintains the date, elapsed heating time and occurrence time of an event or condition (e.g., the time when medical solutions are inserted and/or removed from the system, etc.). The temperature controller may measure the elapsed time or record an occurrence time based on signals received from the heating and/or power supply cabinets, temperature sensors and/or input devices. For example, the temperature controller may initiate measurement of a time interval in response to enablement of the power supply or heating cabinet, and may store the elapsed and/or occurrence time in response to any condition (e.g., when solution or other item is removed). The temperature controller may further measure elapsed time or record elapsed and/or occurrence time in response to medical personnel manually entering information on input devices 146 (e.g., start and stop keys). The temperature controller collects the appropriate information and arranges the information into a report. The report may be arranged in any fashion and include any desired information. Moreover, the report and/or information may be stored in a memory device (e.g., local controller memory, removable memory, card, disk, etc.) for later retrieval as described below. In addition, the temperature controller is coupled to display 112 to display the elapsed (or running) time, report or any desired information to medical personnel. The information displayed may be selected via input devices 146. The report may further be printed via printer 144. The printer and display may be implemented by any conventional or other printer and/or display devices.

The temperature controller memory is used to store the collected information. Basically, the temperature controller logs records containing system information (e.g., the date/time that medical solution is inserted into heating cabinet 4, the date/time that the medical solution is removed from the system, temperatures, etc.). In this manner, use of the system is documented with recorded log entries. Log triggering events can be user defined via input devices 146 that allow the system to be configured to record information in response to a wide variety of detected conditions, continuously, and/or at particular times or periodic intervals. The memory can be used to store a wide variety of information related to use of the system and the memory may alternatively be implemented by an electronic memory chip, a smart card, a floppy disk, a fixed or removable magnetic disk. The temperature controller may be configured to support one or more of those memory storage types.

The information collected and/or recorded by the temperature controller and produced in a report can include, but is not limited to: the date/time that a medical solution was placed into/removed from the heating cabinet, the temperature of the medical solution upon being placed into/removed from the heating cabinet, the temperature of the medical solution at specific points in time while stored in the heating cabinet, start date and time that the medical solution began to be heated, the length of time that the medical solution was heated, the temperature that the medical solution was heated to during the heating cycle and/or the amount of solution or other item residing, placed in or removed from the system. The report may also include related information, such as patient information (e.g., name and identification number), facility information (e.g., name and location), doctor information, the type of procedure, the type of solution or other item being heated, the amount or quantity of fluid or other item being heated (e.g., fluid (or other item) level, volume or weight), the flow rate of fluid that is being heated, the temperature of fluid within the container or fluid line as the fluid is being infused, the pressure of fluid flow as the fluid is heated and any other desired information. The system may employ any type of sensors or sensing devices (e.g., temperature sensors, presence sensors, weight sensors, volume sensors, pressure sensors, flow sensors, fluid sensors, fluid level sensors, etc.) to measure and provide any desired information to the temperature controller for inclusion in a report. The recordation or collection may occur automatically or via user entered information (e.g., start, stop and/or record keys) as described above.

Temperature controller 134 stores and retrieves information from memory in order to produce a report. The report may be transmitted to printer device 144 that is disposed within the power supply cabinet. The report may further be displayed by display 112. The printer basically provides a report in hardcopy form. The temperature controller may control the printer to produce the report at specified times (e.g., termination of heating, at particular times of day, after a particular quantity of uses, etc.) or in response to requests from medical personnel via input devices 146 (e.g., print key). The printer may print the report on any desired hardcopy medium. The printer may place the information onto a label that is attached to a medical file. The information may be printed during or after the solution heating, or be stored on a memory device and printed at a desired time as described above. The printer may further provide additional copies of the report in response to user requests, or a medium automatically creating duplicates may be utilized (e.g., carbon-less paper, etc.).

The report may alternatively be provided in electronic form. The temperature controller may facilitate communication with other devices for transference or downloading of the report to those devices. For example, the information may be downloaded or transmitted over a network or other communications medium to another device (e.g., PDA, computer, another warming system, etc.) for viewing, storage and/or printing.

Information is collected by temperature controller 134 and stored in memory, typically in real-time, as events occur. Reports can be generated and printed/displayed in a timely manner to allow a local or remote (e.g., at a network workstation or computer) user to monitor the status of one or more systems and the status of medical solution undergoing thermal treatment. Alternatively, reports can be generated and printed/displayed at a time of a user choosing. For example, a user either local to or remote from a system is able to monitor the temperature of medical solutions and the time that medical solutions have been stored within a system based upon reports printed or shown on a display device. The user may access stored information relating to one or more systems by requesting (e.g., via temperature controller input devices, a remote workstation, etc.) that a report be produced or displayed to a specific printer or display (e.g., local or remote).

Operation of the temperature controlled infusion system is described with reference to FIGS. 1–4. Specifically, each of the heating and power supply cabinets are secured to a pole or other support structure in the manner described above, and a solution container 18 (e.g., an IV bag) is placed within heating plate 14 and secured therein by cover 16 and hook member 15. Power supply cord 6 is engaged at the power supply ports of each cabinet to facilitate a supply of power from the power supply cabinet to the heating cabinet. Power switch 110 on power supply cabinet 100 is enabled to provide power to system 2, which in turn activates power indicator 41 on heating cabinet 4 (i.e., the power indicator LEDs turn on) to indicate power supply and activation of the heating cabinet. When cover 16 includes bladder 20 (FIG. 2), the bladder may be inflated to provide a desired fluid flow rate as described above. Heating controller 136 is typically set to provide power to heating pad 142 (and to heating element 150, when that heating element is employed) in order to maintain the solution bag at a predetermined temperature as described above. The heating pad may be disposed on one or more of the heating plate panels. For example, the heating pad may be disposed on the heating plate middle panel, while heating plate side panels each conduct heat from the middle panel to evenly heat the solution container. Additionally, heating pads may be disposed on the side panels. Temperature controller 134 monitors the temperature of heating plate 14 via high limit sensor 138 and shuts power off to the heating controller in response to the heating plate temperature attaining excessive levels as described above. Alternatively, temperature information may be entered by the user as described above to control operation of the heating controller and/or temperature controller. Thus, the heating and temperature controllers control power to the heating pad (and heating element) to ensure the solution bag is maintained at the desired temperature prior to and during dispensing of solution from the bag to a patient.

Temperature sensor 40 directly measures the solution bag temperature and may provide the measured information to temperature controller 134 and/or display device 112 to display the solution container temperature. In addition, orientation of the heating cabinet with respect to the IV pole may be easily adjusted by the user by rotating the heating cabinet in a selected direction and to a selected degree about securing pin 34 of support member 30 to permit easy viewing of the front portion of the heating cabinet.

The heating cabinet may further include secondary power source 160, as noted above, for situations in which the heating cabinet must be disconnected from the power supply cabinet during system operation. The secondary power source preferably includes a battery and may be automatically and/or manually engaged or disengaged via user-operable switch 162 in accordance with connection of the power supply cord to the heating cabinet. Thus, the secondary power supply source renders the heating cabinet operable to maintain the solution container at the desired temperature when the heating cabinet is disconnected from the power supply cabinet.

In addition, temperature controller 134 may receive information from the heating cabinet and/or input devices 146 to start measuring a heating time interval and collect report information as described above. The elapsed time or other information may be displayed on display 112 as described above.

Temperature controller 134 may receive appropriate information for a report from the heating cabinet, temperature sensors or other input devices at any time (e.g., before, during or after the session). The temperature controller arranges the information into a desired report as described above. The report may be produced by printer 144, displayed by display 112, or transmitted to another device via a local or network connection as described above. The report may be generated concurrently with system operation (e.g., as data is collected) or in response to termination of a session (e.g., indicated by signals received from the heating cabinet) or a request by medical personnel (e.g., via input devices 146).

It will be appreciated that the embodiments described above and illustrated in the drawings represent only a few of the many ways of implementing a method and apparatus for controlling temperature of infused liquids.

The heating and power supply cabinets may be of any shape or size, and may be constructed of any suitable materials. The cabinets may include housing walls, panels, ledges, projections and/or other structural components that may be of any quantity, shape or size, may be constructed of any suitable materials, and may be attached or connected via any suitable techniques (e.g., fasteners, welding, formed as integral components, etc.). Any number of hook members having any suitable shapes and dimensions may be disposed at any suitable locations on the heating plate or the heating cabinet housing for affixing solution containers in position with the heating plate. Each of the heating and power supply cabinets may further be supported on any type of support structure (e.g., IV or other pole, wall, counter, etc.) and may include any quantity of handles disposed at any suitable locations for facilitating portability. The cabinets may be positioned in any desired orientation for system operation. The support members of the heating and power supply cabinets may be of any suitable type and may have any suitable configuration to facilitate selective orientation of the cabinets with respect to the support structure to which they are secured. The heating and power supply cabinets may include any quantity of any conventional or other cord retracting mechanisms to retract and/or store any system cords (e.g., power supply cord, wall outlet cord, etc.). The retractor mechanisms may be disposed at any suitable locations on and/or within the cabinets.

The cover of the heating cabinet may be of any shape or size and may be constructed of any suitable materials (e.g., flexible, rigid, etc.). The cover is preferably constructed of transparent materials to permit clear viewing of the solution bag, but may alternatively be constructed of any translucent or opaque materials, or any combination of transparent, translucent and opaque materials. Any portion of the cover may be secured to the heating cabinet housing at any locations via any conventional or other fastening techniques (e.g., bolts, screws, adhesives, etc.). Further, any conventional or other fasteners (e.g., hook and loop, hooks, clasps, etc.) may be utilized to removably secure the cover to the heating cabinet housing. The cover may be disposed on the heating cabinet housing in any fashion and open from any direction (e.g., top, bottom, side, etc.) to removably secure the solution bag to the housing. Alternatively, the heating cabinet housing may include a roller type device to engage the cover unsecured end and wind the cover about the roller to retain the solution bag.

The cover may include any quantity of any type of conventional or other heating device (e.g., heating pad, acrylic heater, coils, etc.) to facilitate heating of the solution bag or container. The heating element wiring may be embedded within or disposed on the sheet and/or cover in any fashion and include any configuration suitable to heat the solution bag or container. The terminals may be of any quantity, shape or size, and may be embedded within or disposed on the sheet and/or cover at any suitable locations. The heating element may be formed integral with the cover.

The system may include any combination of heating plates, heating pads and/or heating elements. For example, the system may include any number of heating plates, heating pads and/or heating elements to heat one or more solution bags engaged with the heating cabinet to a desired temperature. The heating plate may include any quantity of heating panels of any shape or size and constructed of any suitable materials. The heating panels may be arranged in any fashion to form any type of heating plate configuration. The heating plate may include any quantity of conventional or other heating devices (e.g., heating pads, resistive wires, etc.) of any shape or size disposed at any suitable locations on the heating plate. The temperature sensors may be implemented by any quantity of any conventional or other type of temperature measuring devices disposed at any suitable locations for measuring the temperature of the heating plate and the solution container or containers engaging the heating cabinet. The system may heat and maintain the solution within the container to any desired temperature or range of temperatures.

The system control circuit may be arranged and disposed in the heating and/or supply cabinets in any fashion, and may include any conventional or other types of fuses (e.g., for any suitable current limit), controllers, switches (e.g., lighted), power supplies and other components. The controllers may each be implemented by any quantity of any conventional or other type of controller, microprocessor, or circuitry capable of collecting the report information for generating the reports and controlling the heating plate, heating element and/or temperature display. Alternatively, the controllers may be implemented by a commercially available controller pre-programmed and loaded with its own software. The controllers may be disposed at any suitable locations on or within the heating and power supply cabinets and include any types of displays, lights or other indicators, or switches (e.g., lighted) arranged in any fashion. Any number of temperature displays may be disposed at any locations on the heating cabinet and/or power supply cabinet and/or be remote from the system and may be implemented by any quantity of any conventional or other types of displays, such as LED or LCD displays. The heating controller and/or the temperature controller may be configured to directly control the heating plate and heating element in response to the measured temperatures and temperatures entered by the user, and disable the heating plate in response to excessive temperatures. The temperature display may display any quantity of digits and/or characters to reflect the actual and set point temperatures or any other desired information. The controllers may include any quantity of any types of input devices (e.g., buttons, keypad, voice recognition, etc.) disposed at any suitable locations on the heating cabinet and/or power supply cabinet to facilitate entry of information and/or selective control of the displays to display any desired information (e.g., desired temperature, actual temperature, temperature limit for the heating plate, etc.).

The power supplies may be implemented by any quantity of conventional or other type of power supply and provide power or voltage signals at any desired levels. The temperature control features of the present invention may be utilized individually and/or in any combination in response to system power and/or actuation of any quantity of any types of switches.

The heating cabinet may be configured to accommodate any quantity of solution bags or other containers of any shape or size. The heating cabinet may further be configured to include any suitable pressure device (e.g., a pressure device similar to the device described in U.S. patent application Ser. No. 09/380,507) to provide pressurized infusion of fluid in combination with maintaining the solution container at a desired temperature. The bellows or bladder may be implemented by any inflatable device capable of expanding upon inflation, and may be inflated via any type of fluid, such as a gas (e.g., air) or liquid. The fluid may be heated in order to inflate the bellows and heat the solution bag. The bellows may be of any shape or size capable of applying pressure to the solution bag, may be constructed of any suitable materials, and may be disposed at any location and/or oriented in any fashion on the cover or within the housing. For example, the bellows may be disposed behind the heating plate and expand to force the heating plate against the solution bag to warm the solution and initiate a desired solution flow rate. The heating plate is typically hinged in this arrangement to transition between expanded and collapsed states in response to inflated and deflated states of the bellows, respectively. Further, any quantity (e.g., at least one) of bellows may be utilized to apply pressure to the solution bag in substantially the same manner described above. The hose for directing fluid to and from the bellows may be implemented by any conventional or other type of hose or tube, may be of any size or shape, and may be constructed of any suitable materials. The gauge for measuring and displaying pressure may be implemented by any conventional or other type of gauge, may be of any size or shape, and may be disposed at any suitable location. The bellows may be inflated by any type of inflating device or pump including any type of valve or other device for controlling inflation and deflation of the bellows.

The power supply cabinet may be configured to simultaneously provide power to any selected number of heating cabinets. The heating and power supply cabinets may further be configured to be compatible and interchangeable with other cabinets of similar design to facilitate the mobility of the cabinets during system operation.

The heating plate may be of any shape or size, be constructed of any suitable materials and include any quantity of heating panels of any shape or size. The heating plate and/or heating panels may be arranged in any fashion to form any type of heating plate configuration. The heating plate may include any quantity of conventional or other heating devices (e.g., heating pads, resistive wires, etc.) of any shape or size disposed at any suitable locations on the heating plate. The temperature sensor may be implemented by any quantity of any conventional or other type of temperature measuring devices disposed at any locations on the heating plate. Alternatively, a temperature sensor may be disposed in contact with the solution bag to directly measure a solution temperature.

The system may include devices to record any types of information relating to system operation for subsequent retrieval, analysis, display and reports (e.g., date and time of thermal treatment disablement and enablement, fluid level or use, temperature, etc.). The system may employ any type of sensors or sensing devices (e.g., temperature sensors, presence sensors, weight sensors, volume sensors, pressure sensors, flow sensors, fluid sensors, fluid level sensors, etc.) to measure and provide any desired information to the temperature controller for inclusion in a report. The temperature controller may maintain the date, elapsed heating time and/or occurrence time of any event or condition (e.g., time medical solution is inserted and/or removed within system, etc.). The temperature controller may measure the elapsed time or record an occurrence time for any desired condition. The temperature controller may maintain the time information internally or utilize any desired external circuitry (e.g., a timer, etc.). Further, a separate controller may be used for information collection and reports.

The temperature controller may collect any desired information (e.g., start date and time of solution or other item heating, the time interval the solution or other item was heated, the temperature the solution or other item attained during heating, temperature of the solution or other item when the solution was removed from the system, amount or quantity of solution or other item residing, placed in or removed from the system, partial or complete history of time and solution or other item temperature measured at any desired time intervals, facility name and location, patient information, doctor information, type of procedure, type of solution, amount or quantity of solution or other item being heated, etc.) from any desired sources (e.g., user, memory device, another computer or device, etc.). The temperature and/or other sensors may be coupled to the temperature controller either individually or in any combination or fashion.

The reports may be arranged in any fashion and include any desired information. The date, time and other information may be in any desired format (e.g., month, day and year, hours and minutes, text, numeric, icons, etc.). The report information may be arranged and/or presented (e.g., printed, displayed, etc.) in any desired formats (e.g., text, charts, graphs, columns, rows, tables, etc.) and in any order or arrangement. The graph may include any quantity of axes each associated with any desired information (e.g., time, temperature, etc.) in any desired scales or units (e.g., Celsius, Fahrenheit, etc.). The graphs may utilize any types of symbols or characters (e.g., dots, diamonds, dashes, alphanumeric characters, punctuation symbols, etc.) to indicate points on the graph. The graphs may indicate time, temperature or events (e.g., removal of solution, etc.) in any fashion. The reports may provide information (e.g., temperature, etc.) measured or collected continuously or at any desired preset or user specified time intervals (e.g., hours, minutes, seconds, etc.). The time intervals may be specified by a user via any input devices (e.g., input devices (e.g., keys, buttons, etc.), remote or local computer, etc.). The report and/or information may alternatively be stored in a local or remote database or memory device (e.g., local memory, removable memory, etc.) for later retrieval. The reports may include a pre-arranged format or may be programmable or selected by a user via input devices. The temperature display may be of any quantity, shape or size, may be disposed at any location on or remote from the system, may be implemented by any conventional or other displays (e.g., LED, LCD, etc.) and may display any desired information. The information displayed may be selected via controller input devices, or the display may include display controls (e.g., buttons, keys, etc.).

The printer may be implemented by any conventional or other printing device, may be local or remote, may serve any quantity of systems or other devices, and may produce reports on any desired medium (e.g., paper, labels, etc.). The heating cabinet may include a printer and/or display to provide information to a user. The slot for providing a hardcopy report may be defined at any suitable locations on or within the heating and/or power supply cabinets. The reports may be printed and/or displayed concurrently with system operation as report data is collected or at any specific time or in response to user entered information (e.g., a print command or key). The report may be printed at any desired time before, during or after system use, and may be retrieved from the system at any desired time or in any desired manner. The system or temperature controller may include any conventional or other communications device or module (e.g., modem, etc.) and may download or transfer an electronic form of the report to any desired device (e.g., PDA, computer, another system, etc.) at any specific time or in response to user entered information (e.g., transmit command or key). Systems may further be networked to enable retrieval of reports and/or information from a station coupled to the network. The printer and display may be disposed at any suitable locations on or remote from the system. Alternatively, the systems may be implemented to generate reports without the printer and/or display. Any desired information may be transmitted between the system components (e.g., temperature controller, printer, display, etc.) via any conventional or other communications medium or protocols (e.g., hardwire, wireless, network, etc.).

Software for the temperature, heating and report controllers may be implemented in any desired computer language and could be developed by one of ordinary skill in the computer arts based on the functional descriptions contained herein. The temperature, heating and report controllers may be implemented by any type of processors, hardware and/or other processing circuitry, and may be available pre-programmed for immediate use. The various functions of the temperature and heating controllers may be distributed in any manner among any quantity of software and/or hardware modules, processors and/or circuitry.

The power supply and heating cabinets may be formed as a single or integral unit, or be distributed among any quantity of units. Further, any conventional or other types of coupling devices or media (e.g., cables, wires, wireless, etc.) may be used to couple the cabinets or units or the components thereof.

The present invention is not limited to the applications disclosed herein, but may be utilized for infusion of any fluids (e.g., saline, blood, antibiotics or other drugs, gases, irrigation fluids, etc.).

It is to be understood that the terms "top", "bottom", "front", "rear", "side", "height", "width", "length", "upper", "lower" and the like are used herein merely to describe points of reference and do not limit the present invention to any particular configuration or orientation.

From the foregoing description, it will be appreciated that the invention makes available a novel method and apparatus for controlling temperature of infused liquids, wherein a bag or container of an IV fluid is secured to the heating plate of a portable heating cabinet via a flexible cover and the heating cabinet receives power from a power supply cabinet to facilitate temperature control of the fluid during infusion from the container to a patient.

Having described preferred embodiments of a new and improved method and apparatus for controlling temperature of infused liquids, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A system for controlling temperature of medical solutions, wherein power supply units reside at different sites, the system comprising:
   a power supply unit including a power supply housing and a power supply connector, said power supply unit for attachment to a support structure;
   a heating unit to receive and heat a medical solution, wherein said heating unit is portable and removably coupled to said power supply unit for operation with other power supply units at said different sites, said heating unit including:
   a heater housing;
   a heating plate recessed within said heater housing to heat said medical solution;
   a cover to wrap around at least a portion of a container containing said medical solution to secure said container against said heating plater; and
   a heater power connector removably coupled to said power supply connector to transfer power between said power supply and said heater power connectors.

2. The system of claim 1, wherein said heating unit further includes a power indicator to indicate when power is received from said power supply unit.

3. The system of claim 1 further including an input device to facilitate entry of a desired temperature for said medical solution.

4. The system of claim 1, further including a controller to control heating of said medical solution.

5. The system of claim 4, wherein said heating unit further includes:
- at least one heating pad disposed proximate said heating plate to apply heat to at least a portion of said heating plate;
- a heating pad controller to control said at least one heating pad to apply heat to said heating plate; and
- a threshold temperature sensor coupled to said controller to measure temperature of said heating plate;
- wherein said controller disables said heating pad controller in response to said threshold temperature sensor measuring a heating plate temperature exceeding a threshold temperature.

6. The system of claim 4, further including:
- a temperature sensor to measure a temperature of said medical solution, wherein said temperature sensor is coupled to said controller.

7. The system of claim 6, wherein said controller includes:
- a collection module to collect information including the time and temperature of said medical solution.

8. The system of claim 7, wherein said controller further includes:
- a report module to generate a report including a history of medical solution temperature.

9. The system of claim 8, wherein said controller further includes:
- a communication module to transmit at least one of said collected information and said report to a remote device.

10. The system of claim 8 further including a display to display at least one of said medical solution temperature, said time and said report.

11. The system of claim 8 further including a printing device to print said report.

12. The system of claim 1, wherein said heating plate includes a generally curved configuration to conform to said container to provide heat to a plurality of container surfaces.

13. The system of claim 1, wherein said heating unit further includes a secondary power source to facilitate operation of said heating unit when said heating unit is disconnected from said power supply unit.

14. The system of claim 1, wherein said cover is a flexible cover that wraps around at least a portion of said container containing said medical solution.

15. The system of claim 1, wherein said cover includes a heating element to heat said container.

16. The system of claim 1, wherein said cover includes an inflatable device to apply pressure to said container to produce a desired medical solution flow rate.

17. The system of claim 1 further including:
- a power cord to couple said power supply and heating units; and
- a power outlet cord to couple said power supply unit to a power source;
- wherein at least one of said power supply unit and said heating unit includes a cord retractor mechanism to retract and store at least one of said power cord and said power outlet cord.

18. The system of claim 1, wherein said heating unit further includes a securing member to secure said heating unit to said support structure.

19. The system of claim 18, wherein said securing member includes a rotation member to rotate said heating unit relative to said support structure to a desired orientation.

20. The system of claim 19, wherein said rotation member includes a swivel mechanism.

21. The system of claim 20, wherein said rotation member includes a ratcheting mechanism.

22. The system of claim 6, wherein said controller controls heating of said medical solution in accordance with said measured medical solution temperature.

23. A method of controlling temperature of medical solutions, wherein power supply units reside at different sites, the method comprising:
- (a) receiving a medical solution within a heating unit including a heater housing, wherein said heating unit includes a heater power connector and is portable and removably coupled to a power supply unit secured to a support structure, the power supply unit including a power supply housing and a power supply connector removably coupled to said heater power connector to transfer power between said power supply and said heater power connectors, said heating unit for operation with other power supply units at said different sites;
- (b) securing a container containing said medical solution within said heating unit via a cover that wraps around at least a portion of said container; and
- (c) heating said medical solution via a heating plate recessed within a heating unit housing, wherein said container is secured against said heating plate by said cover.

24. The method of claim 23, wherein step (a) further includes:
- (a.1) indicating when power is received by said heating unit from said power supply unit via a power indicator.

25. The method of claim 23, wherein step (a) further includes:
- (a.1) facilitating entry of a desired temperature for said medical solution via an input device.

26. The method of claim 23, wherein step (c) further includes:
- (c.1) applying heat to at least a portion of said heating plate via at least one heating pad disposed proximate said heating plate;
- (c.2) measuring temperature of said heating plate; and
- (c.3) disabling said heating pad in response to a measured heating plate temperature exceeding a threshold temperature.

27. The method of claim 23, wherein step (c) further includes:
- (c.1) measuring a temperature of said medical solution.

28. The method of claim 27, wherein step (c) further includes:
- (c.2) collecting information including the time and temperature of said medical solution.

29. The method of claim 28, wherein step (c) further includes:
- (c.3) generating a report including a history of medical solution temperature.

30. The system of claim 29, wherein step (c) further includes:
- (c.4) transmitting at least one of said collected information and said report to a remote device.

31. The method of claim 29, wherein step (c) further includes:
- (c.4) displaying at least one of said medical solution temperature, said time and said report on a display.

32. The method of claim 29, wherein step (c) further includes:
(c.4) printing said report via a printer.

33. The method of claim 23, wherein step (c) further includes:
(c.1) heating said medical solution via said heating plate with a generally curved configuration to conform to said container to provide heat to a plurality of container surfaces.

34. The method of claim 23, wherein step (c) further includes:
(c.1) facilitating operation of said heating unit via a secondary power source when said heating unit is disconnected from said power supply unit.

35. The method of claim 23, wherein said cover includes a heating element, and step (c) further includes:
(c.1) heating said medical solution via said heating plate and said heating element.

36. The method of claim 23, wherein said cover includes an inflatable device, and step (c) further includes:
(c.1) applying pressure to said container via said inflatable device to produce a desired medical solution flow rate.

37. The method of claim 23, wherein said heating and power supply units are associated with at least one cord to couple said power supply and heating units and to couple said power supply unit to a power source, and step (a) further includes:
(a.1) retracting and storing at least one of said coupling cord and said power cord via a cord retractor mechanism disposed within at least one of said power supply unit and said heating unit.

38. The method of claim 23, wherein said heating unit further includes a securing member to secure said heating unit to said support structure, and wherein said securing member includes a rotating member to rotate said heating unit relative to said support structure and step (b) further includes:
(b.1) rotating said heating unit relative to said support structure to a desired orientation via said rotating member.

39. The method of claim 27, wherein step (c) further includes:
(c.2) controlling heating of said medical solution in accordance with said measured medical solution temperature.

40. A system for controlling temperature of medical solutions, comprising:
a housing;
a heating plate recessed within said housing to heat said medical solution;
a flexible cover to wrap around at least a portion of a container containing said medical solution to secure said container against said heating plate;
a temperature sensor to measure a temperature of said medical solution; and
a controller to control heating of said medical solution, wherein said controller is coupled to said temperature sensor and includes:
a collection module to collect information including the time interval the solution was heated and temperature of said medical solution.

41. The system of claim 40, wherein said controller further includes:
a report module to generate a report including a history of medical solution temperature.

42. The system of claim 40, wherein said controller further includes:
a communication module to transmit at least one of said collected information and said report to a remote device.

43. The system of claim 40 further including a display to display at least one of said medical solution temperature, said time interval and said report.

44. The system of claim 40 further including a printing device to print said report.

45. A method of controlling temperature of medical solutions comprising:
(a) receiving a medical solution within a heating unit;
(b) securing a container containing said medical solution within said heating unit via a flexible cover that wraps around at least a portion of said container; and
(c) heating said medical solution via a heating plate recessed within a heating unit housing, wherein said container is secured against said heating plate by said flexible cover and step (c) further includes:
(c.1) measuring a temperature of said medical solution; and
(c.2) collecting information including the time interval the solution was heated and temperature of said medical solution.

46. The method of claim 45, wherein step (c) further includes:
(c.3) generating a report including a history of medical solution temperature.

47. The method of claim 46, wherein step (c) further includes:
(c.4) transmitting at least one of said collected information and said report to a remote device.

48. The method of claim 46, wherein step (c) further includes:
(c.4) displaying at least one of said medical solution temperature, said time interval and said report on a display.

49. The method of claim 46, wherein step (c) further includes:
(c.4) printing said report via a printer.

* * * * *